US008858446B2

(12) United States Patent
Sato

(10) Patent No.: US 8,858,446 B2
(45) Date of Patent: Oct. 14, 2014

(54) COLOR DOPPLER ULTRASONIC DIAGNOSIS APPARATUS WHICH CAN CALCULATE BLOOD FLOW COMPONENT INFORMATION

(75) Inventor: Takeshi Sato, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 619 days.

(21) Appl. No.: 12/971,669

(22) Filed: Dec. 17, 2010

(65) Prior Publication Data

US 2011/0152689 A1 Jun. 23, 2011

(30) Foreign Application Priority Data

Dec. 21, 2009 (JP) ................................ 2009-289634

(51) Int. Cl.
*A61B 8/00* (2006.01)
*A61B 8/06* (2006.01)
*A61B 8/08* (2006.01)
*A61B 8/13* (2006.01)

(52) U.S. Cl.
CPC ................ *A61B 8/5238* (2013.01); *A61B 8/06* (2013.01); *A61B 8/488* (2013.01); *A61B 8/0891* (2013.01); *A61B 8/08* (2013.01); *A61B 8/13* (2013.01)
USPC ......................................... 600/454; 600/437

(58) Field of Classification Search
USPC ........... 600/453–458; 382/128, 276, 260–265
See application file for complete search history.

(56) References Cited

U.S. PATENT DOCUMENTS

| 5,477,858 | A | * | 12/1995 | Norris et al. ................... 600/441 |
| 7,736,314 | B2 | * | 6/2010 | Beach et al. ................... 600/437 |
| 2005/0222506 | A1 | * | 10/2005 | Takimoto et al. ............. 600/455 |
| 2009/0209861 | A1 | | 8/2009 | Nishigaki et al. |

FOREIGN PATENT DOCUMENTS

JP 2953083 7/1999

OTHER PUBLICATIONS

Kargel et al. Adaptive Clutter Rejection filtering in Ultrasonic Strain-Flow Imaging. IEEE Trans Ultrason Ferroelectr Freq Control. 50(7):824-835. Jul. 2003.*
Office Action issued Aug. 31, 2012 in Chinese Patent Application No. 201010598546.3.
Hans Torp et al., "Velocity Matched Spectrum Analysis: A New Method for Suppressing Velocity Ambiguity in Pulsed-Wave Doppler", Ultrasound in Med. & Biol., vol. 21, No. 7., 1995, pp. 937-944.

* cited by examiner

Primary Examiner — Parikha Mehta
(74) Attorney, Agent, or Firm — Oblon, Spivak, McClelland, Maier & Neustadt, L.L.P.

(57) ABSTRACT

According to one embodiment, a color Doppler ultrasonic diagnosis apparatus includes an ultrasonic probe, a transmission/reception unit, a quadrature phase detection unit configured to perform quadrature phase detection of an output from the transmission/reception unit, a filter unit configured to perform first orthogonal transformation for an output from the quadrature phase detection unit in a depth direction, perform second orthogonal transformation for a result obtained by the first orthogonal transformation in an ensemble direction, apply a two-dimensional filter to obtained frequency data to extract a blood flow component from the frequency data, and sequentially perform inverse transformation of the second orthogonal transformation and inverse transformation of the first orthogonal transformation for an output from the two-dimensional filter, and a blood flow component information calculation unit configured to calculate blood flow component information based on an output from the filter unit.

12 Claims, 11 Drawing Sheets

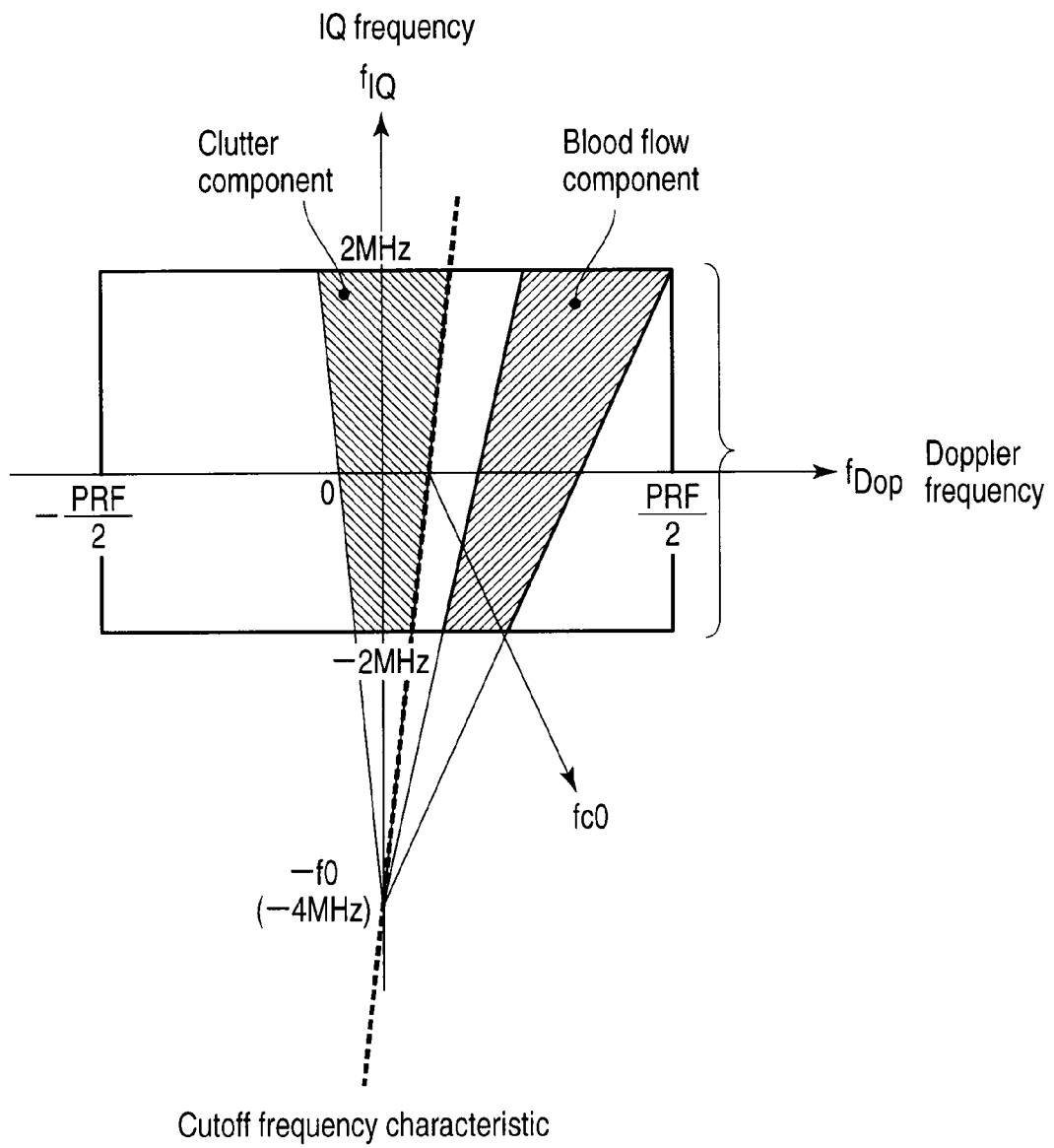
F I G. 3

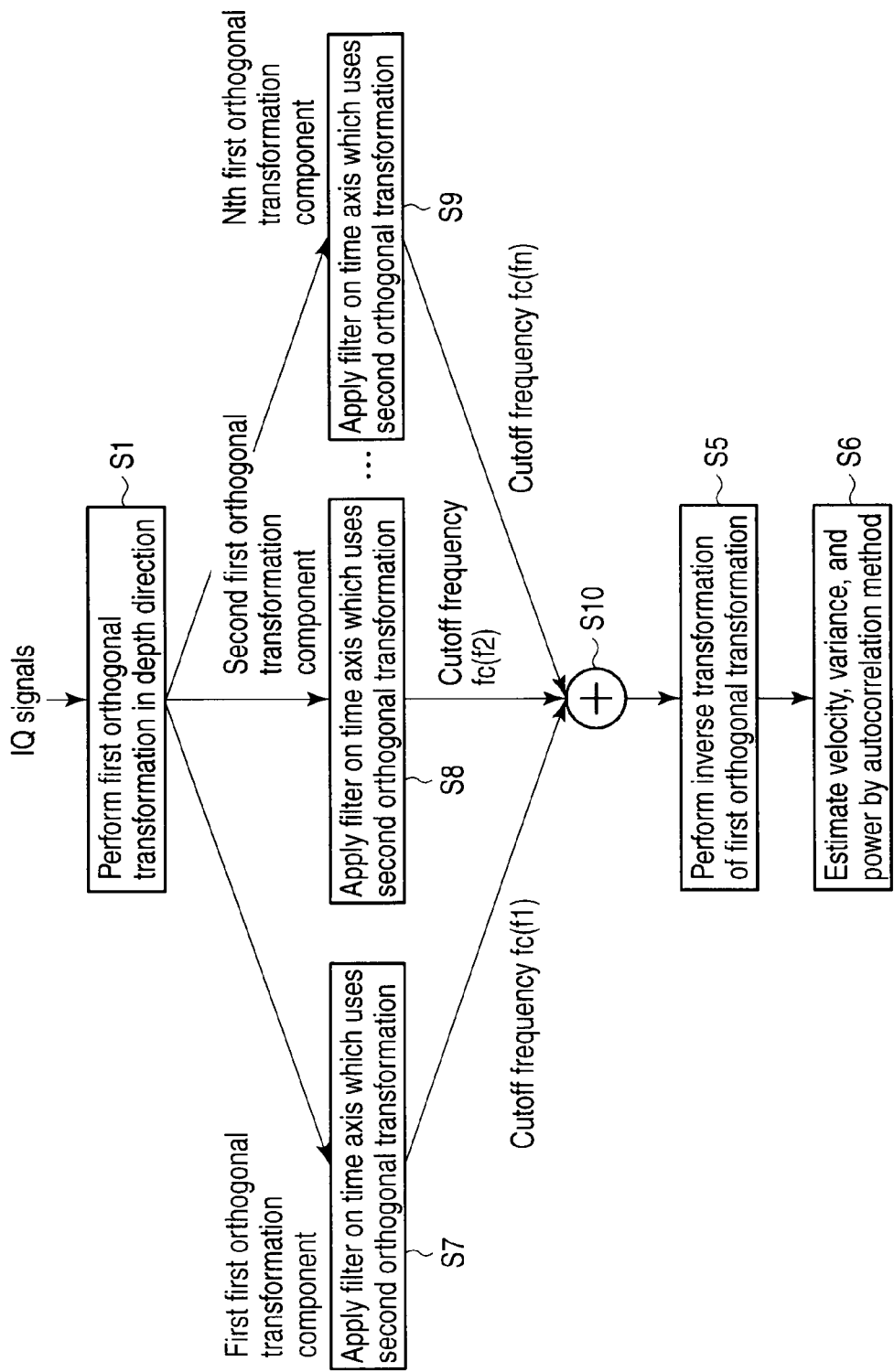
F I G. 4

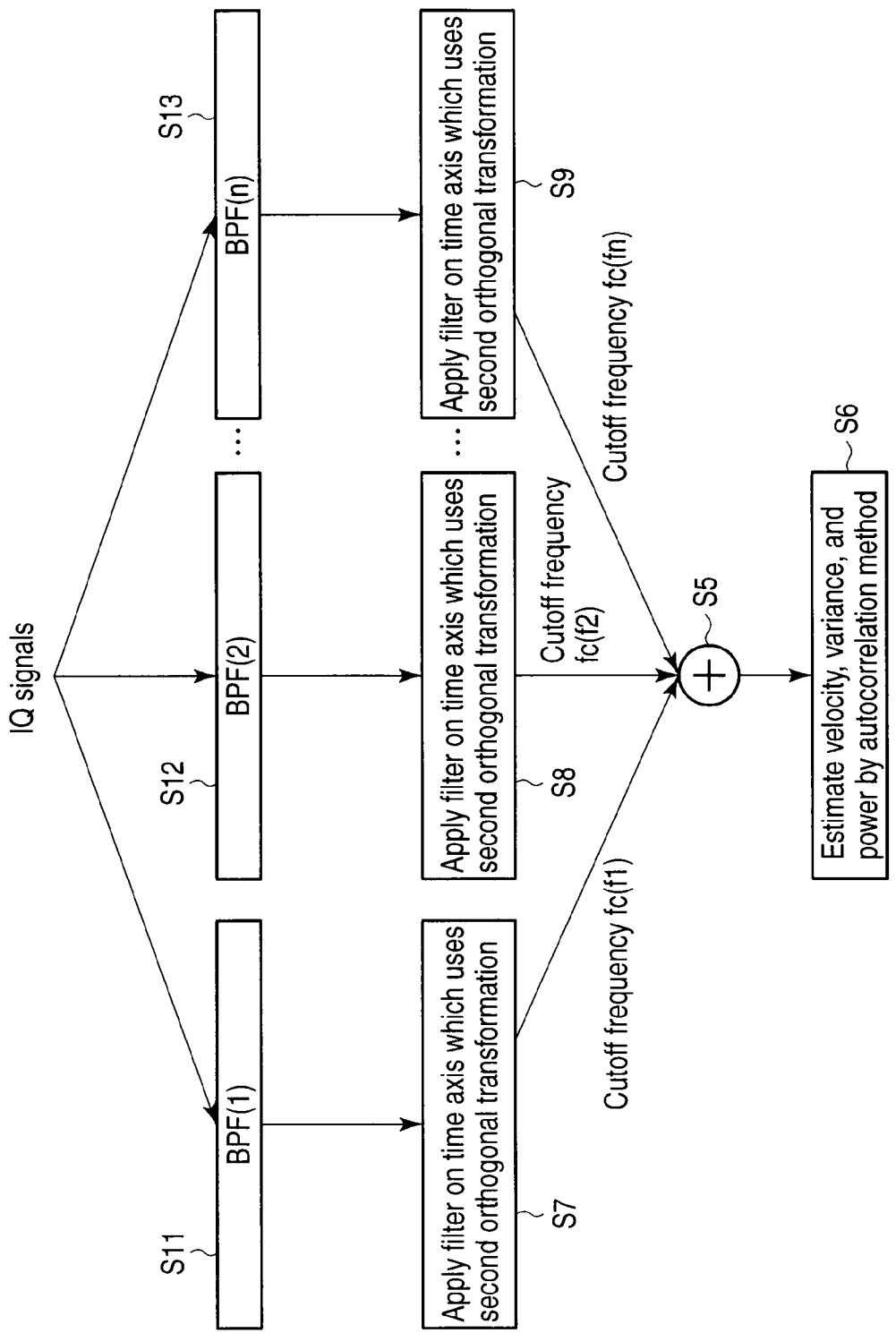
F I G. 5

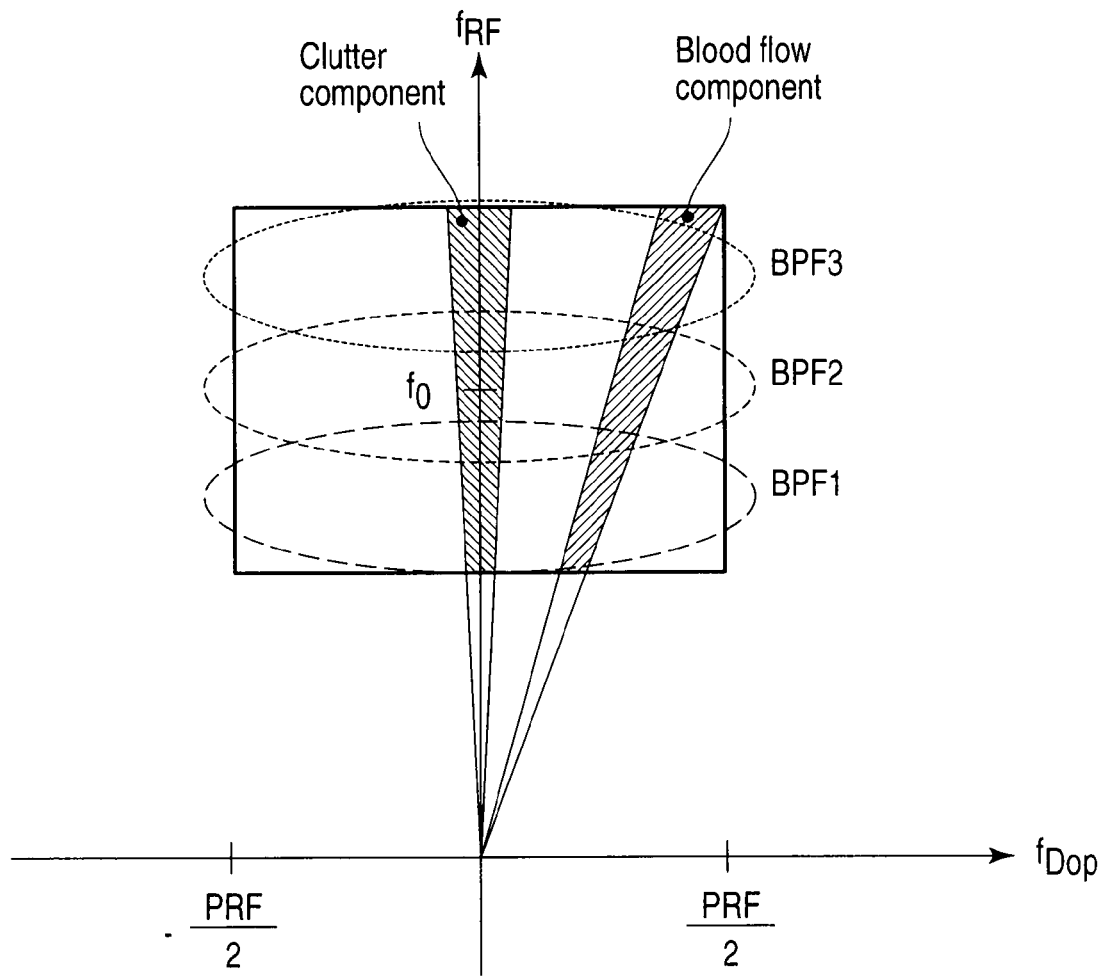
F I G. 6

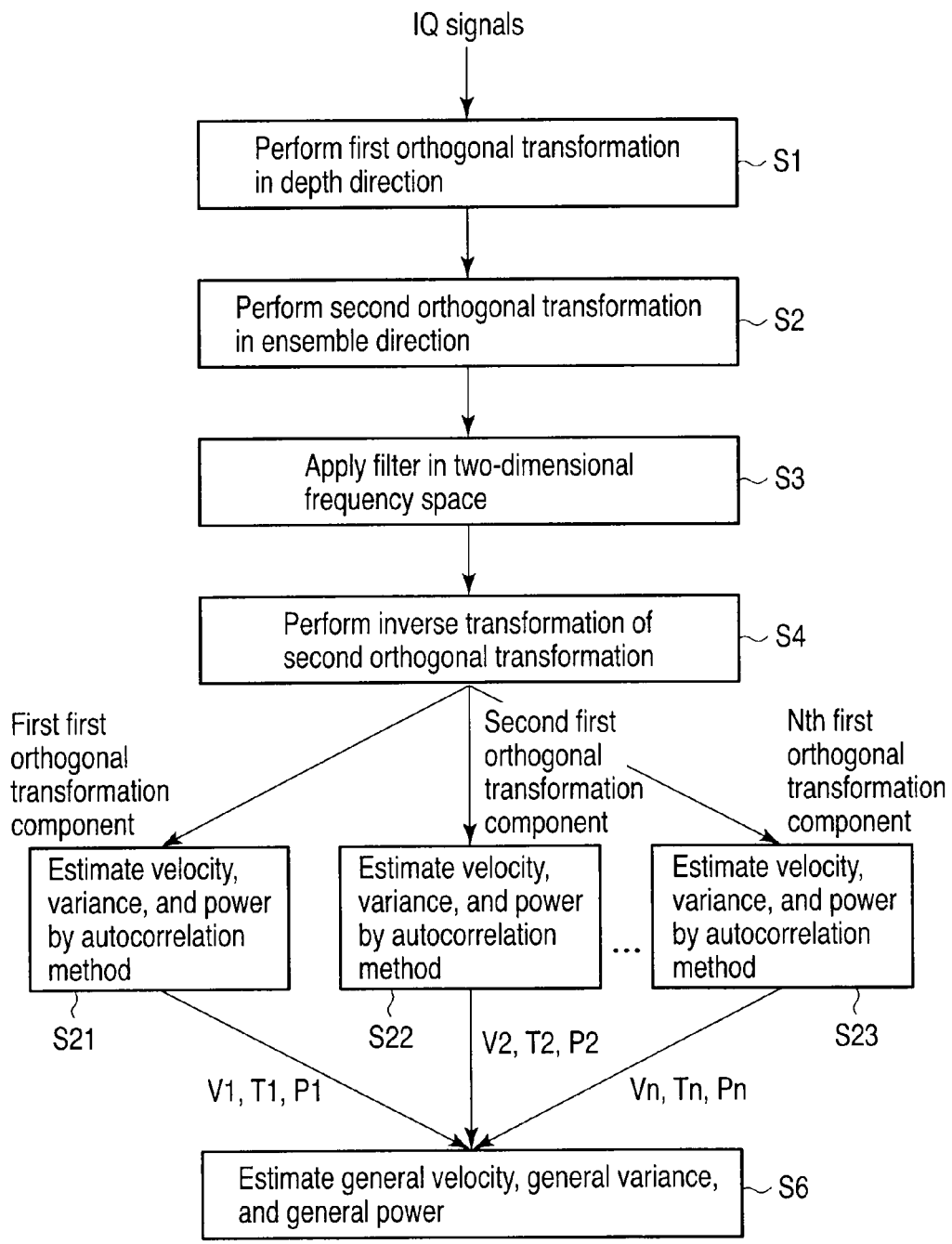
F I G. 7

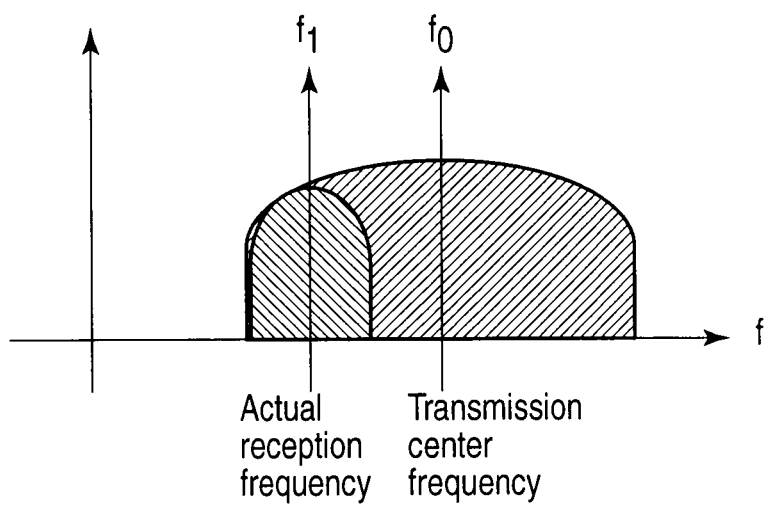
F I G. 13

COLOR DOPPLER ULTRASONIC DIAGNOSIS APPARATUS WHICH CAN CALCULATE BLOOD FLOW COMPONENT INFORMATION

CROSS-REFERENCE TO RELATED APPLICATIONS

This application is based upon and claims the benefit of priority from Japanese Patent Application No. 2009-289634, filed Dec. 21, 2009; the entire contents of which are incorporated herein by reference.

FIELD

Embodiments described herein relate generally to a color Doppler ultrasonic diagnosis apparatus.

BACKGROUND

A color Doppler method in ultrasonic diagnosis extracts blood flow component information by shifted frequencies due to the Doppler effect upon irradiating a living body with ultrasonic waves a plurality of number of times in the same direction. Blood flow component information includes a blood flow velocity, power, and variance. For example, as shown in FIG. 11, this method applies ultrasonic waves in the same direction (to the same raster) N times at a period of 1/PRF (PRF: Pulse Repetition Frequency). The data string in which N echo components corresponding to the same direction and same depth are arrayed along the time axis is called an ensemble direction or Doppler direction. The depth direction is also called the distance direction. Ensemble data is Fourier-transformed, thereby obtaining Doppler frequencies.

The intensity of a tissue signal (clutter component signal) is higher than the signal intensity of blood flow components by about 40 to 100 dB. In order to extract blood flow components flowing in the tissue, it is necessary to suppress tissue signals. A high-pass filter called a wall filter suppresses clutter components. An apparatus is required to have an S/N of 100 dB or more.

A living body has frequency-dependent attenuation. Even when ultrasonic waves are transmitted in a wide band, the center of an echo signal has a low-frequency band. This makes it difficult to use the energy of ultrasonic waves with a high S/N ratio at the time of reception even when they are transmitted in a wide band. For this reason, in color Doppler imaging which requires a high S/N ratio, ultrasonic waves are transmitted in a narrow band.

Recently developed apparatuses have achieved high S/N ratios. Even in color Doppler imaging, such apparatuses can finely express blood flow components in a wide band as in B-mode imaging even when ultrasonic waves are transmitted in a wide band. A wider band is effective in improving distance resolution.

In the color Doppler mode, however, the following problem arises when ultrasonic waves are transmitted in a wide band.

Letting $f_{RF}$ be the frequency of an ultrasonic wave and c be the velocity of sound, when a reflector moves in a direction to approach the probe at a constant velocity v, a frequency $f_{Dop}$ of the resultant Doppler shift is given by $$f_{Dop} = \frac{2v}{c} f_{RF} \quad (1)$$

That is, since the Doppler frequency is proportional to the transmission frequency of an ultrasonic wave, for example, the Doppler frequency obtained by a 2-MHz ultrasonic wave differs twice from the Doppler frequency obtained by a 4-MHz ultrasonic wave. The graph on FIG. 12 shows the relationship between the ultrasonic frequency and the Doppler frequency. The abscissa represents the Doppler frequency; and the ordinate, the ultrasonic transmission frequency. Assume that the amplitude of a Doppler signal at a given Doppler frequency and ultrasonic frequency is expressed by the third axis (not shown) perpendicular to the above two axes. Both the Doppler frequency of a blood flow component and the Doppler frequency of a clutter component are proportional to an ultrasonic frequency.

The prior art performs signal processing for only a Doppler frequency. For this reason, the frequency axes on the above portion of FIG. 12 are integrated into one, and signal processing is then performed for a signal in which blood flow components partially overlap clutter components. The abscissa of the lower graph of FIG. 12 represents the Doppler frequency; and the ordinate, the amplitude of a Doppler signal. That is, although the blood flow components are separated from the clutter components, their Doppler frequencies overlap on the frequency axis, which cannot be separated from each other.

In narrow-band transmission/reception, which has been conventionally used, since only frequencies near a center frequency $f_0$ of a transmission ultrasonic frequency exist, the Doppler frequencies of blood flow components and clutter components do not overlap. However, when ultrasonic waves are transmitted/received in a wide band, the Doppler frequency components of blood flow components and clutter components may overlap. In such a case, a wall filter cannot separate clutter components from blood flow components, resulting in an image containing many clutter components.

In addition, when ultrasonic waves are transmitted in a wide band with the center frequency $f_0$, an actual reception signal is influenced by frequency-dependent attenuation in the living body and is received at a frequency $f_1$ lower than $f_0$. In general, however, $f_1$ cannot be known. Equation (1) is therefore rewritten into $$v = \frac{2}{c} \frac{f_{RF}}{f_{Dop}} \quad (2)$$

In equation (2), since $f_{RF}$ is unknown, it is not possible to obtain a correct velocity v. In transmission/reception of ultrasonic waves in a narrow band, which has conventionally been used, since the transmission frequency $f_0$ is almost equal to the reception frequency $f_1$, such a problem has not arisen.

Patent reference 1 discloses a method using two types of ultrasonic transmission/reception frequencies. This patent reference discloses the method of estimating a velocity exceeding an aliasing velocity by using different ultrasonic transmission/reception frequencies and the fact that blood flow components with the same velocity differ in Doppler frequency. However, the reference has no mention of a technique of separating clutter components from blood flow components.

BRIEF DESCRIPTION OF THE DRAWINGS

FIG. 3 is a view showing an example of the two-dimensional frequency characteristic of a quadrature-detected complex signal (IQ signal) output from a reception circuit in FIG. 1;

FIG. 4 is a flowchart showing a processing procedure by the first modification of the first embodiment;

FIG. 5 is a flowchart showing a processing procedure by the second modification of the first embodiment;

FIG. 6 is a graph showing the relationship between three types of passbands in a BPF in FIG. 5;

FIG. 7 is a flowchart showing a processing procedure for a two-dimensional filter unit according to the second embodiment;

FIG. 13 is a graph showing reception frequencies having undergone frequency-dependent attenuation in a living body, together with transmission frequencies.

DETAILED DESCRIPTION

In general, according to one embodiment, a color Doppler ultrasonic diagnosis apparatus includes an ultrasonic probe, a transmission/reception unit configured to transmit/receive an ultrasonic wave to/from an object via the ultrasonic probe, a quadrature phase detection unit configured to perform quadrature phase detection of an output from the transmission/reception unit, a filter unit configured to perform first orthogonal transformation for an output from the quadrature phase detection unit in a depth direction, perform second orthogonal transformation for a result obtained by the first orthogonal transformation in an ensemble direction, apply a two-dimensional filter to obtained frequency data to extract a blood flow component from the frequency data, and sequentially perform inverse transformation of the second orthogonal transformation and inverse transformation of the first orthogonal transformation for an output from the two-dimensional filter, and a blood flow component information calculation unit configured to calculate blood flow component information based on an output from the filter unit.

This embodiment will be described below with reference to the views of the accompanying drawing.

Figure 1:
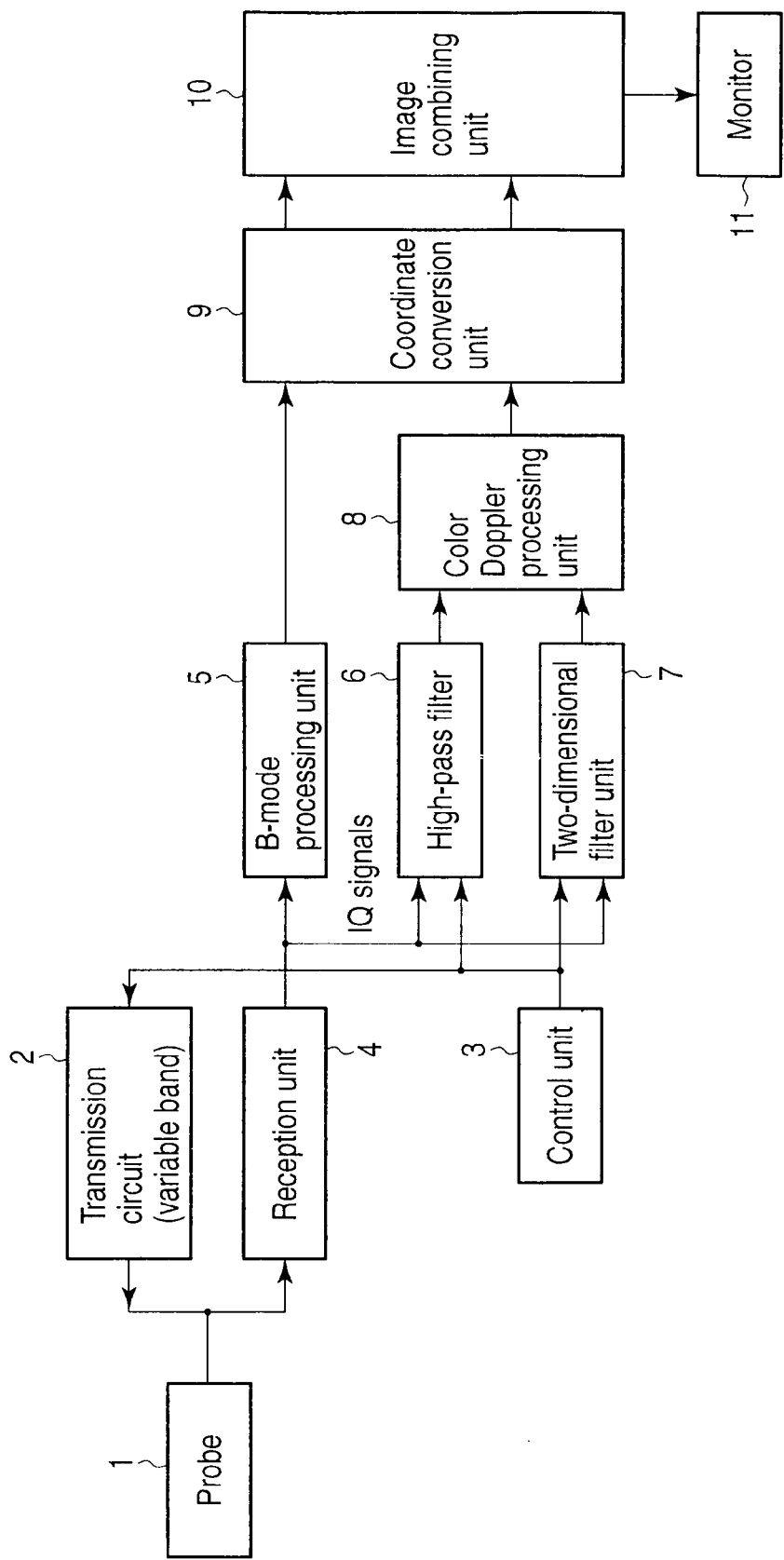
FIG. 1 is a block diagram showing the arrangement of a color Doppler ultrasonic diagnosis apparatus according to the first embodiment.

FIG. 1 shows the arrangement of a color Doppler ultrasonic diagnosis apparatus according to the first embodiment. An ultrasonic probe 1 includes a plurality of piezoelectric transducers. An acoustic matching layer is provided on the front side of the piezoelectric transducers. A backing member or the like is provided on the rear side of the piezoelectric transducers. The plurality of piezoelectric transducers are arrayed two-dimensionally or three-dimensionally to allow electrical two-dimensional or three-dimensional scanning. A transmission circuit 2 applies pulse signals to the piezoelectric transducers of the probe 1 to generate ultrasonic waves. The piezoelectric transducers of the ultrasonic probe 1 convert ultrasonic echoes from the object into electrical signals.

The transmission circuit 2 is configured to switch the band of transmission ultrasonic waves between a relatively wide band and a relatively narrow band under the control of a control unit 3. In the B mode, ultrasonic waves in a relatively wide band are selected. In the first color Doppler mode, ultrasonic waves in a relatively narrow band are selected. In the second color Doppler mode, ultrasonic waves in a relatively wide band are selected. The band used in the second color Doppler mode may be wider than that used in the B mode. Note that the band selected in the first color Doppler mode is equal to that in the conventional color Doppler mode. In the first color Doppler mode, a bandpass filter similar to that in the prior art separates clutter components from blood flow components. In the second color Doppler mode, a two-dimensional filter characteristic to this embodiment separates clutter components from blood flow components. This operation will be described in detail later.

An increase in the band of ultrasonic waves will be described below. The reciprocal of a transmission frequency $f_0$ is a transmission period $T_0$. An ultrasonic pulse having a time length corresponding to one ultrasonic period $T_0$, an ultrasonic pulse having a time length corresponding to two periods "$2 \cdot T_0$", and an ultrasonic pulse having a time length corresponding to M periods "$M \cdot T_0$" are respectively referred to as a one-wave burst pulse, a two-wave burst pulse, and a three-wave burst pulse. One wave, two waves, ..., M waves will be referred to as burst wave numbers. A pulse length is equivalent to the value obtained by multiplying a transmission period by a burst wave number. Typically, a wide band is generated by ultrasonic waves having the transmission frequency $f_0$ and a burst wave number M of less than 3. A narrow band is generated by ultrasonic waves having the transmission frequency $f_0$ and a burst wave number M of 3 or more. Note that a wide band is not necessarily defined by only pulses having a burst wave number of less than 3. For example, a wide band may be defined by a ratio "$\Delta W/T$" of a half width $\Delta W$ on the envelope of a burst wave to a period T. When this ratio is used, a wide band is defined by "$\Delta W/T$"=2.2 or less. In addition, the range of a wide band may be defined by specific band of spectrum of ultrasonic wave=$\Delta W/fc$ ($\Delta W$: half width and fc: spectrum center frequency). In this case, specific band=$\Delta W/fc$=0.3 or more corresponds to a "wide band".

The ultrasonic waves transmitted from the ultrasonic probe 1 to the object P are sequentially reflected by the discontinuity surface of acoustic impedance of an internal body tissue. The ultrasonic probe 1 receives an echo signal. The amplitude of this echo depends on an acoustic impedance difference on the discontinuity surface by which the ultrasonic waves have been reflected. The echo produced when a transmitted ultrasonic pulse is reflected by a moving blood flow or a surface such as a cardiac wall is subjected to a frequency shift depending on the velocity component of the moving body in the ultrasonic transmission direction due to a Doppler effect.

The transmission circuit 2 includes a pulse generator, transmission delay circuit, and pulser. The pulse generator repetitively generates rate pulses for the formation of transmission ultrasonic waves at a predetermined rate frequency fr Hz (period: 1/fr sec). The transmission delay unit gives each rate pulse a delay time necessary to focus an ultrasonic wave into a beam and determine transmission directivity for each channel. The pulse generator applies a driving pulse to the probe 1 at the timing based on this rate pulse for each channel.

A reception unit 4 includes a preamplifier, A/D converter, reception delay unit, adder, and quadrature phase detection circuit. The preamplifier amplifies echo signals received via the probe 1 for each channel. The reception delay unit gives each amplified echo signal the delay time required to determine a reception directivity. The adder then performs addition processing. With this addition, the reflection component of the echo signal from the direction corresponding to reception directivity is enhanced, and a synthetic beam for ultrasonic transmission/reception is formed in accordance with the reception directivity and transmission directivity. The quadrature phase detection circuit functions in the first and second color Doppler modes. The quadrature phase detection circuit mixes an echo signal with a reference signal in phase with the transmission ultrasonic wave, and also mixes the echo signal with a reference signal $\pi/2$ out of phase with the transmission ultrasonic wave. The quadrature phase detection signals will be referred to as IQ signals hereinafter.

A B-mode processing unit 5 generates the data of a B-mode image from an echo signal from the reception unit 4 by logarithmic amplification, envelope detection processing, and the like.

A high-pass filter 6 and a two-dimensional filter unit 7 are connected to the output of the reception unit 4. In the first color Doppler mode, the high-pass filter 6 functions under the control of a control unit 3. In the second color Doppler mode, the two-dimensional filter unit 7 functions under the control of the control unit 3. The high-pass filter 6 is a one-dimensional high-pass filter on the time axis, which is called a wall filter like that used in the prior art. This filter suppresses clutter components and extracts blood flow components. The two-dimensional filter unit 7 will be described later.

A color Doppler processing unit 8 extracts a shift frequency based on a Doppler effect of an echo signal received from the high-pass filter 6 or the two-dimensional filter unit 7, and extracts mainly blood flow components from a moving object, thereby obtaining blood flow data such as an average velocity, variance, and power at each of multiple points. A coordinate conversion unit 9 called a digital scan converter (DSC) converts the coordinate system of a blood flow image such as an average velocity image, variance image, or power image, which corresponds to an ultrasonic scanning procedure, into a general orthogonal coordinate system. An image combining unit 10 combines a blood flow image with a B-mode image. A monitor 11 displays the resultant image.

The two-dimensional filter unit 7 will be described in detail below. The two-dimensional filter unit 7 in this embodiment can separate blood flow components from clutter components even if a wide band which does not allow the high-pass filter 6 to separate blood flow components from clutter components is selected. The high-pass filter 6 allows only one-dimensional observation with Doppler frequencies. However, conceiving two-dimensional filtering with an ultrasonic frequency and a Doppler frequency can separate blood flow components from clutter components which cannot be separated by the high-pass filter 6.

According to this embodiment, the apparatus performs the first orthogonal transformation in the depth direction, and performs the second orthogonal transformation in the packet direction for Doppler detection, thereby dividing the reception signal into two-dimensional orthogonal space components. The apparatus then applies a filter to the components to separate them into blood flow components and clutter components on the two-dimensional space. The first orthogonal transformation is performed by multiplying a reception signal by a window function and then performing discrete Fourier transformation. The second orthogonal transformation is performed by performing transformation such as discrete Fourier transformation, transformation to an orthogonal polynomial space, discrete cosine transformation, or Karhunen-Loeve transformation. After applying a filter on the two-dimensional space, the apparatus performs the inverse transformation of the second orthogonal transformation to restore all the components to those on the time axis. The color Doppler processing unit 8 then estimates a velocity, power, and variance. The processing performed by the color Doppler processing unit 8 is common to the first and second color modes. The apparatus can estimate a velocity, power, and variance for each band of ultrasonic frequencies without performing the inverse transformation of the first orthogonal transformation. The apparatus can also estimate a velocity with higher accuracy by using the fact that the velocity is proportional to the ultrasonic frequency.

In wide-band transmission/reception, the color Doppler ultrasonic diagnosis apparatus according to this embodiment can separate blood flow components from clutter components, which cannot be separated with Doppler frequencies viewed from a one-dimensional direction, by additionally using an ultrasonic frequency as another dimension. This can suppress clutter components in an image including many clutter components in the conventional method.

In addition, in wide-band transmission/reception, it is generally difficult to know a reception center frequency because of frequency-dependent attenuation in a living body. This makes it difficult to estimate an accurate velocity value. However, the scheme of this embodiment obtains a velocity value by dividing a reception signal for each frequency, and hence can estimate an accurate velocity value. Furthermore, this can estimate a velocity higher than an aliasing velocity.

As described above, this apparatus separates the IQ signal, generated by causing the quadrature phase detection circuit of the reception unit 4 to mix a reception signal with the frequency $f_0$, into clutter components and blood flow components in the manner shown in FIG. 3.

Figure 2:
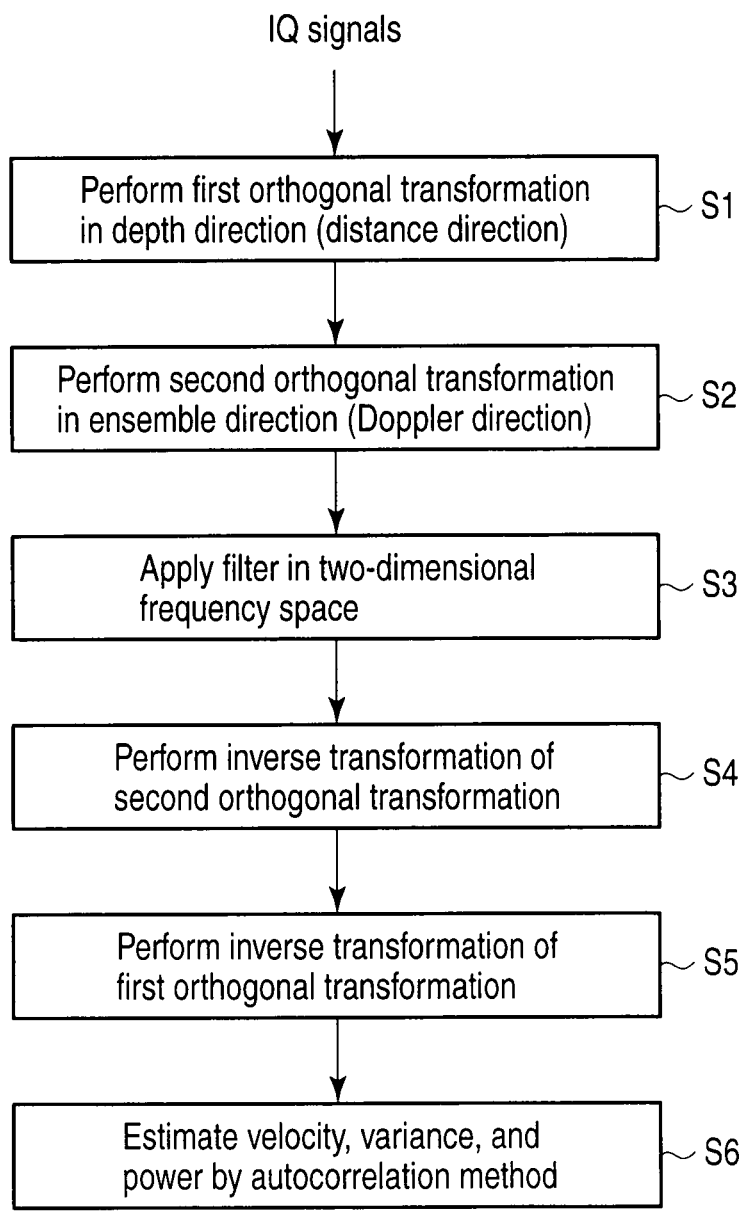
FIG. 2 is a flowchart showing a processing procedure for a two-dimensional filter unit in FIG. 1.

As shown in FIG. 2, first of all, the apparatus performs the first orthogonal transformation in the depth direction (S1). The apparatus then performs the second orthogonal transformation for the first orthogonal transformation result in the ensemble direction (S2). If both the first and second orthogonal transformations are discrete Fourier transformations, the result obtained is that shown in FIG. 3. When the cutoff frequency of the wall filter is represented by $f_{c0}$ on the Doppler frequency axis at the RF frequency $f_0$, i.e., an IQ frequency 0, the apparatus forms a high-pass filter (S3) which has a cutoff frequency $f_c(f)$ at an IQ frequency $f$ which is given by $$fc(f) = \frac{f_{c0}}{f_0}(|f| + f_0) \quad (3)$$

Referring to FIG. 3, this filter cuts the clutter portion. In this case, the "filter" means processing on the frequency axis. That is, this processing is to multiply each two-dimensional frequency component by a proper coefficient. In order to restore the respective components to the time domain, the apparatus performs the inverse transformation of the second orthogonal transformation first (S4). The apparatus then performs the inverse transformation of the first orthogonal transformation (S5). After obtaining IQ signals by removing the clutter components from the signal in this manner, the apparatus can estimate the velocity, variance, and power of the signal by the autocorrelation method using the same technique as that in the prior art (S6).

If the first and second orthogonal transformations are discrete Fourier transformations, each transformation may be performed by two-dimensional discrete Fourier transformation instead of one-dimensional transformation. Two-dimensional discrete Fourier transformation can also be used as inverse transformation. In the case of discrete Fourier transformation, since a window function is required before transformation, transformation is performed after multiplication by a predetermined window function.

In general, there are only about 6 to 20 data in the ensemble direction. Performing discrete Fourier transformation by multiplying data with such a small data size by a window function will degrade the sensitivity of blood flow components. Furthermore, discrete Fourier transformation cannot theoretically separate low-frequency components beyond an observation time, and hence cannot sufficiently remove clutter components constituted by low-frequency components.

For this reason, the apparatus performs transformation based on an orthogonal polynomial space as the second orthogonal transformation. An orthogonal polynomial uses the polynomial obtained by multiplying a Legendre polynomial by proper coefficients as an orthogonal basis. A method of forming a wall filter by using an orthogonal polynomial space is disclosed in the following reference: Steinar Bjaerum and Hans Torp, "Clutter filter design for ultrasound color flow imaging", IEEE Transaction on ultrasonics, ferroelectrics, and frequency control, Vol. 49, No. 2, pp. 204-216, February, 2002.

A merit of an orthogonal polynomial space is that since the polynomial need not be a periodic function, no window function is required. In addition, since a linear coefficient is a linear component, it is possible to detect slowly moving clutter components which can be approximated to a straight line having a certain gradient within the observation time. It is therefore possible to remove such slowly moving clutter components. This orthogonal space is different from a Fourier frequency space, and hence cannot be expressed as in FIG. 6. However, using Z transformation allows easy association of frequencies in an orthogonal polynomial space (in this case, the results obtained by orthogonal transformation will be referred to as frequencies; frequencies in the usual sense will be referred to as Fourier frequencies) with frequencies in a Fourier space. It is possible to effectively remove clutter components by applying a filter having a cutoff frequency $f_c(f)$ on the Fourier frequency axis to the two-dimensional space of "Fourier frequencies in depth direction+orthogonal polynomial frequencies in ensemble direction" in accordance with this association.

In addition, discrete cosine transformation can be used as the second orthogonal transformation. Since discrete cosine transformation is not assumed to use any periodic function, no window function is required. As the second orthogonal transformation, Karhunen-Loeve transformation can be used. Karhunen-Loeve transformation is a method of decomposing a signal into orthogonal components including the maximum main component based on the statistical nature of the signal. Since orthogonal transformation always accompanies inverse transformation, it is possible to restore the frequency components on the frequency axis in the orthogonal space to those on the original time axis by applying a filter to them on the frequency axis and performing inverse transformation.

FIG. 4 shows a procedure for the first modification of the first embodiment. The first modification differs from the first embodiment in that the apparatus applies a filter to each frequency of the first orthogonal transformation output for each distance, without performing the second orthogonal transformation (S2), so as to apply a filter equivalent to that on the frequency axis in the second orthogonal space onto the time axis (S7, S8, and S9). According to this scheme, the apparatus performs discrete Fourier transformation in the depth direction as the first orthogonal transformation, adds the outputs obtained by applying a wall filter (wall filter on the time axis) in the prior art to the respective frequencies while changing the cutoff frequency (S10), and then performs discrete inverse Fourier transformation for the resultant output. The processing in the first embodiment is mathematically equivalent to that in the first modification.

Figure 10:
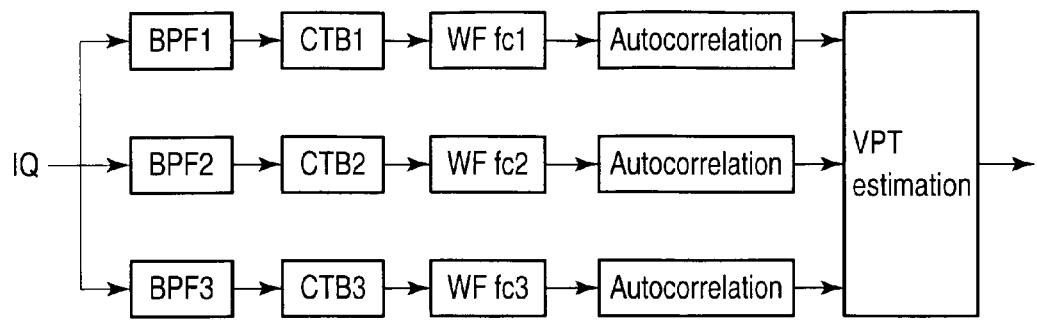
FIG. 10 is a block diagram showing the arrangement of a two-dimensional filter unit according to the second modification of the first embodiment.
Figure 11:
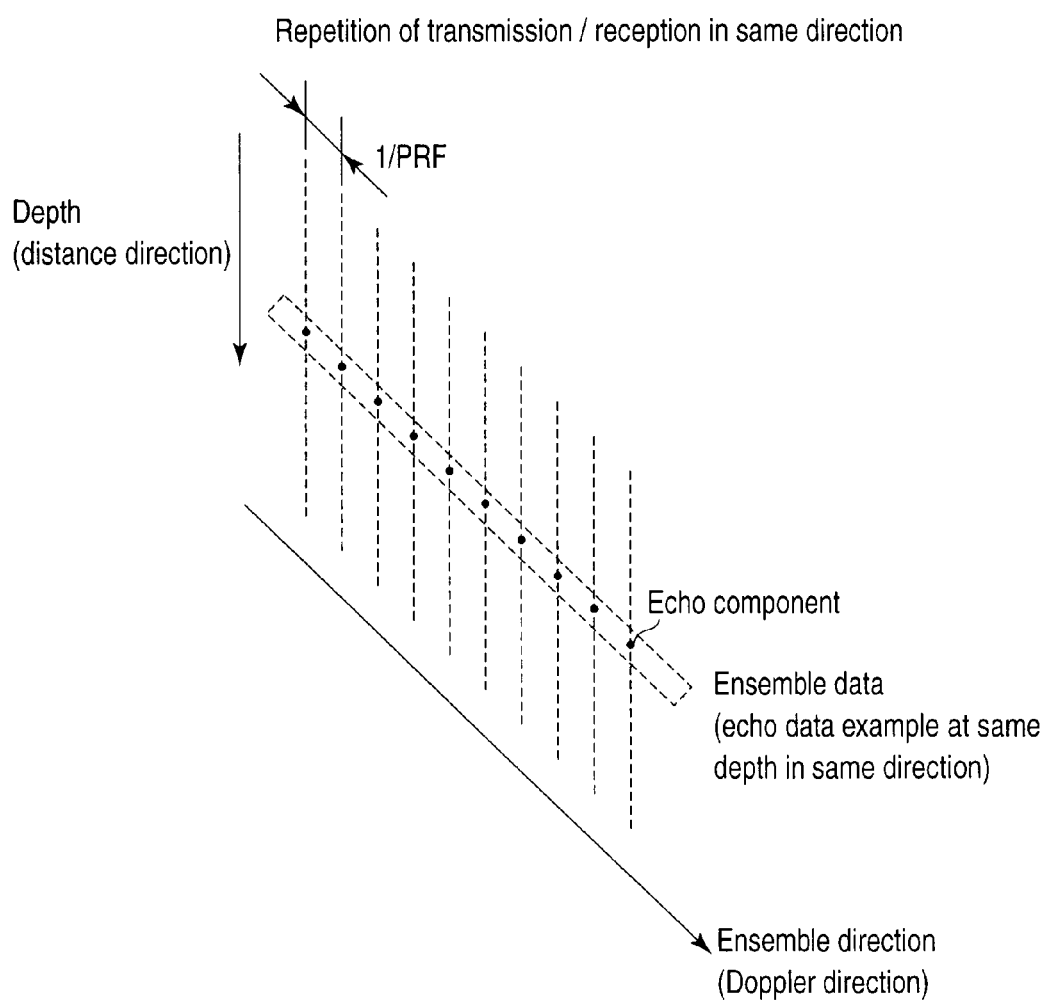
FIG. 11 is a view showing a packet.
Figure 12:
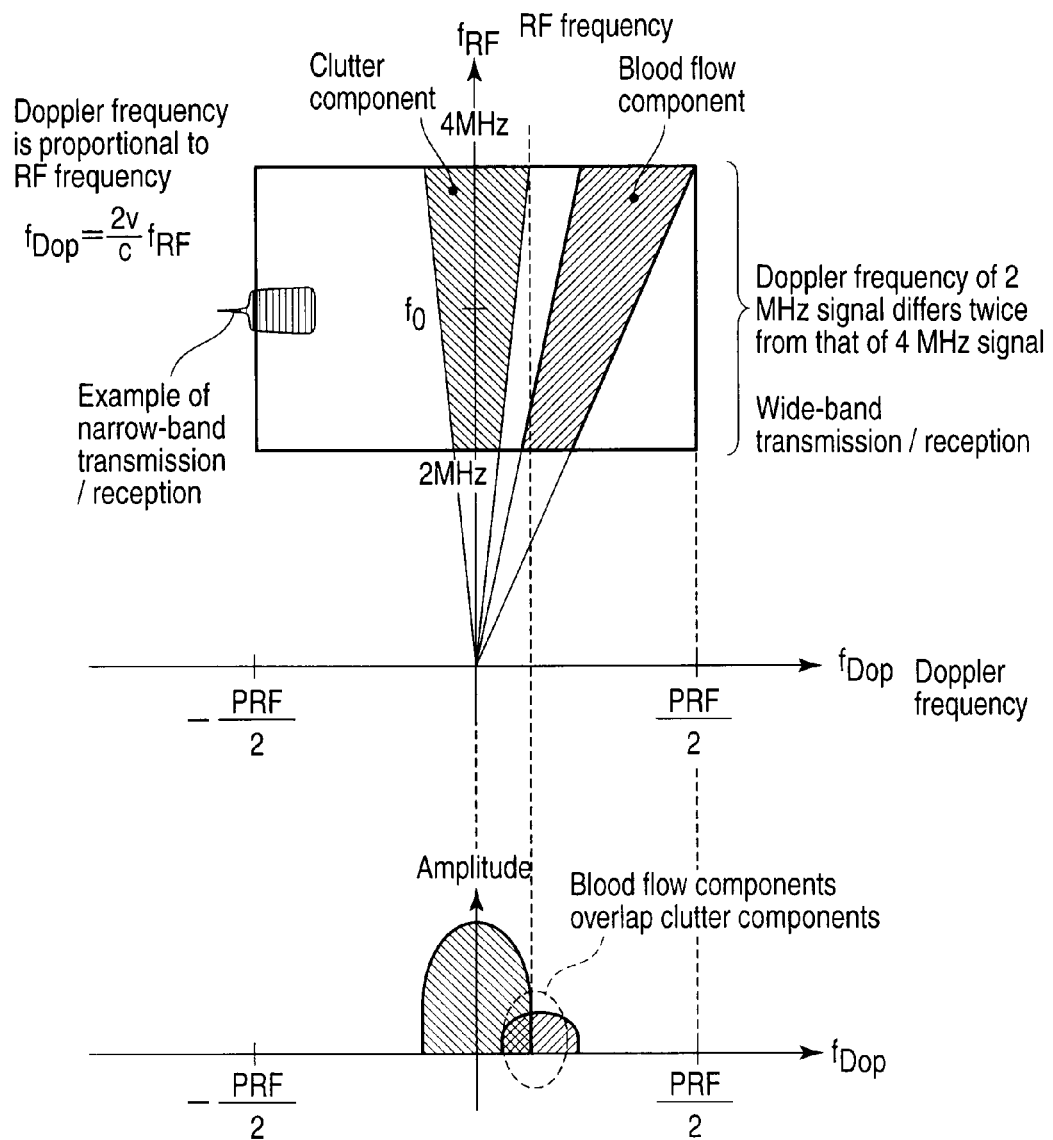
FIG. 12 is a view showing the problem that when ultrasonic waves are transmitted/received in a wide band, a conventional bandpass filtering technique cannot separate clutter components from blood flow components.

FIG. 5 shows a procedure for the second modification of the first embodiment. The second modification differs from the first embodiment in that both the first and second orthogonal transformations (S1 and S2) are processing on the time axis. As shown in FIGS. 6 and 10, the apparatus divides IQ signals into groups of frequency bands in the first orthogonal transformation for each distance by using a plurality of bandpass filters (BPFs) having different passbands (S11, S12, and S13). The apparatus performs the processing as that in the first modification of the first embodiment for the divided signals. FIG. 6 shows this state on the frequency axis.

Second Embodiment

The arrangement of the second embodiment is the same as that of the first embodiment. FIG. 7 shows a procedure for two-dimensional filtering according to the second embodiment. The processing up to the execution of the inverse transformation of the second orthogonal transformation (S1 to S4) is the same as that in the first embodiment.

After performing the inverse transformation of the second orthogonal transformation, the apparatus does not execute the inverse transformation of the first orthogonal transformation. The apparatus then estimates the velocity, variance, and power of each frequency component without transforming them on the first frequency axis (S21, S22, and S23). A velocity, variance, and power are parameters on the Doppler frequency axis, and hence can be estimated by the same processing as that in the first embodiment.

Figure 8:
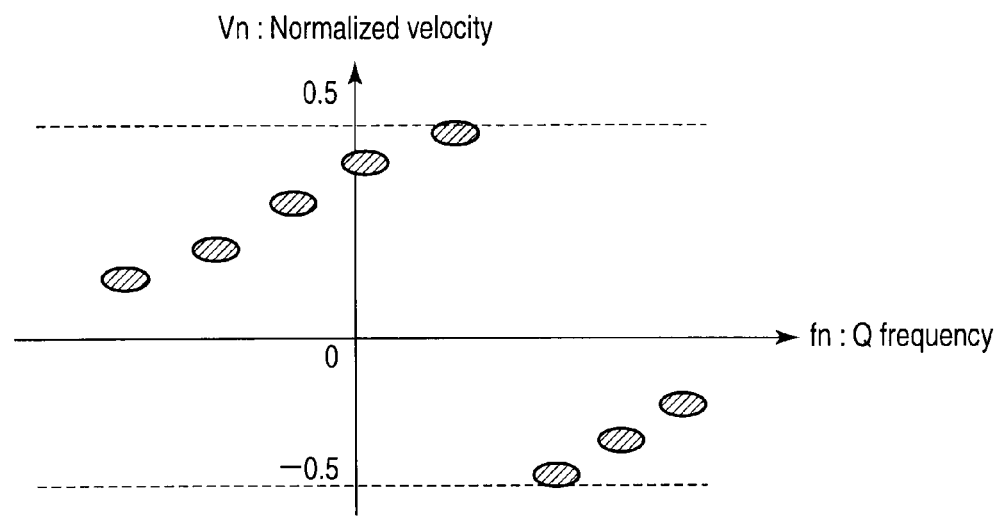
FIG. 8 is a graph showing the relationship between a Fourier frequency fn and a velocity Vn in the first orthogonal transformation in FIG. 7.
Figure 9:
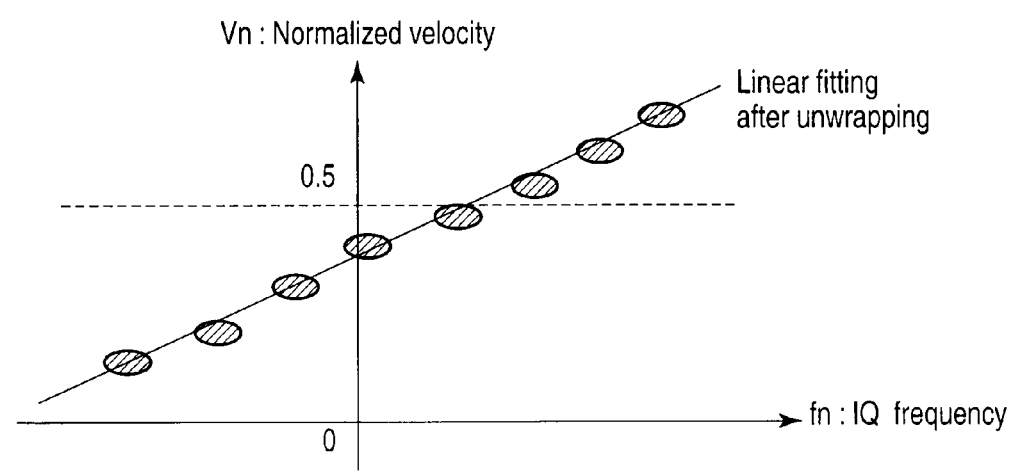
FIG. 9 is a graph showing the velocity Vn after aliasing unwrapping in FIG. 8.

Assume that the first orthogonal transformation in this case is discrete Fourier transformation. Note that there is no limitation on the technique for second orthogonal transformation, and it is possible to use an arbitrary orthogonal transformation technique. Assume that when the Fourier frequency of the first orthogonal transformation is represented by fn, a velocity Vn, variance Tn, and power Pn have been obtained. Note, however, that the velocity Vn is obtained when the autocorrelation function argument is normalized in the range of −0.5 to +0.5. When fn and Vn are plotted on a graph, aliasing like that shown in FIG. 8 occurs. FIG. 9 shows the result obtained by connecting the velocity components upon aliasing unwrapping. Assume that as the gradient of the straight line in FIG. 9, a value a is obtained by the least squares method. In this case, dividing both the sides of equation (1) by PRF will obtain a normalized velocity expressed by $fRF=f_0+f_n$ $$v_n = \frac{2v}{c \cdot PRF}(f_0 + f_n) \qquad (4)$$

Therefore, a gradient a of the straight line in FIG. 9 is given by $$a = \frac{2v}{c \cdot PRF} \quad (5)$$

This makes it possible to obtain a velocity v by $$v = \frac{a \cdot c \cdot PRF}{2} \quad (6)$$

The velocity v is obtained by the least squares method from the velocity obtained from each Doppler frequency obtained by dividing a reception echo in a wide band into echoes in narrow bands. The velocity obtained in this manner is higher in accuracy than that obtained directly from a Doppler signal in a wide band. At the same, it is possible to obtain a velocity higher than an aliasing velocity. That is, the final velocity, variance, and power are obtained from the gradient of the straight line obtained by the least squares method from the velocity value for each Fourier frequency. Referring to FIG. 8, it is possible to properly obtain a high flow velocity to the extent that unwrapping can be properly done.

As the first and second modifications of the second embodiment, there can be provided methods implemented by replacing the blocks after "applying the filter on the time axis using the second orthogonal transformation" in the first and second modifications of the first embodiment by the blocks after "estimating a velocity, variance, and power by the autocorrelation method" in the second embodiment.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A color Doppler ultrasonic diagnosis apparatus comprising:
    an ultrasonic probe;
    a transmission/reception circuit configured to transmit/receive an ultrasonic wave to/from an object via the ultrasonic probe;
    a quadrature phase detection circuit configured to perform quadrature phase detection of an output from the transmission/reception unit;
    a filter configured to perform a first orthogonal transformation for an output from the quadrature phase detection circuit in a depth direction, perform a second orthogonal transformation for a result obtained by the first orthogonal transformation in an ensemble direction, extract a blood flow component from the frequency data using a two-dimensional filter, and to sequentially perform an inverse transformation of the second orthogonal transformation and an inverse transformation of the first orthogonal transformation for an output from the two-dimensional filter; and
    a blood flow component information calculation unit configured to calculate blood flow component information based on an output from the filter.

2. The apparatus according to claim 1, wherein the first orthogonal transformation and the second orthogonal transformation are discrete Fourier transformations.

3. The apparatus according to claim 1, wherein the filter is configured to simultaneously perform inverse transformations of the first orthogonal transformation and the second orthogonal transformation by discrete two-dimensional Fourier transformation and discrete two-dimensional inverse Fourier transformation.

4. The apparatus according to claim 1, wherein the filter is configured to perform discrete Fourier transformation as the first orthogonal transformation and perform Fourier transformation to an orthogonal polynomial space as the second orthogonal transformation.

5. The apparatus according to claim 1, wherein the filter is configured to perform discrete Fourier transformation and discrete cosine transformation as the first orthogonal transformation and the second orthogonal transformation, respectively.

6. The apparatus according to claim 1, wherein the filter is configured to perform discrete Fourier transformation and Karhunen-Loeve transformation as the first orthogonal transformation and the second orthogonal transformation, respectively.

7. A color Doppler ultrasonic diagnosis apparatus comprising:
    an ultrasonic probe;
    a transmission/reception circuit configured to transmit/receive an ultrasonic wave to/from an object via the ultrasonic probe;
    a quadrature phase detection circuit configured to perform quadrature phase detection of an output from the transmission/reception circuit;
    a filter configured to perform an orthogonal transformation for an output from the quadrature phase detection circuit in a depth direction, extract blood flow components by applying filters on a time axis which have different filter characteristics to a result of the orthogonal transformation, and perform an inverse transformation of the orthogonal transformation for outputs from the filters; and
    a blood flow component information calculation unit configured to calculate blood flow component information based on an output from the filter.

8. A color Doppler ultrasonic diagnosis apparatus comprising:
    an ultrasonic probe;
    a transmission/reception circuit configured to transmit/receive an ultrasonic wave to/from an object via the ultrasonic probe;
    a quadrature phase detection circuit configured to perform quadrature phase detection of an output from the transmission/reception circuit;
    a filter being configured to apply a bandpass filter to an output from the quadrature phase detection circuit in a depth direction and being configured to apply filters on a time axis which have different filter characteristics to an output of the bandpass filter in an ensemble direction to extract a blood flow component from the result; and
    a blood flow component information calculation unit configured to calculate blood flow component information based on an output from the filter.

9. A color Doppler ultrasonic diagnosis apparatus comprising:
- an ultrasonic probe;
- a transmission/reception circuit configured to transmit/receive an ultrasonic wave to/from an object via the ultrasonic probe;
- a quadrature phase detection circuit configured to perform quadrature phase detection of an output from the transmission/reception circuit;
- a filter configured to perform first a orthogonal transformation for an output from the quadrature phase detection circuit in a depth direction, perform a second orthogonal transformation for a result of the first orthogonal transformation in an ensemble direction, to extract a blood flow component by applying a two-dimensional filter to obtained frequency data, and perform inverse transformation of the second orthogonal transformation for an output from the two-dimensional filter; and
- a blood flow component information calculation unit configured to calculate blood flow component information based on a frequency component obtained by the first orthogonal transformation and output from the filter.

10. A color Doppler ultrasonic diagnosis apparatus comprising:
- an ultrasonic probe;
- a transmission/reception circuit configured to transmit/receive an ultrasonic wave to/from an object via the ultrasonic probe;
- a quadrature phase detection circuit configured to perform quadrature phase detection of an output from the transmission/reception circuit;
- a filter configured to perform a first orthogonal transformation for an output from the quadrature phase detection circuit in a depth direction, perform a second orthogonal transformation for a result obtained by the first orthogonal transformation in an ensemble direction, extract a blood flow component by applying a two-dimensional filter to obtained frequency data, and perform an inverse transformation of the second orthogonal transformation for an output from the two-dimensional filter; and
- a blood flow component information calculation unit configured to estimate blood flow component information including a velocity, variance, and power of a component generated by the first orthogonal transformation based on an output from the filter and estimate a final velocity, variance, and power based on the estimated velocity, variance, and power.

11. The apparatus according to claim 10, wherein the calculation unit estimates blood flow component information including a blood flow velocity, and a final velocity of the blood flow velocity is obtained from a gradient of a straight line which is obtained from a velocity value for each Fourier frequency by a least squares method.

12. A color Doppler ultrasonic diagnosis apparatus comprising:
- an ultrasonic probe;
- a transmission/reception circuit configured to transmit/receive an ultrasonic wave to/from an object via the ultrasonic probe;
- a quadrature phase detection circuit configured to perform quadrature phase detection of an output from the transmission/reception circuit;
- a filter configured to apply a bandpass filter to an output from the quadrature phase detection circuit in a depth direction and being configured to extract a blood flow component by applying filters on a time axis which have different filter characteristics to an output of the bandpass filter in an ensemble direction; and
- a blood flow component information calculation unit configured to estimate blood flow component information including a velocity, variance, and power with respect to each band based on an output from the filter unit and estimate a final velocity, variance, and power based on the estimated velocity, variance, and power.

* * * * *